(12) United States Patent  
Chin

(10) Patent No.: US 6,972,028 B2
(45) Date of Patent: *Dec. 6, 2005

(54) METHOD OF COOLING AN ORGAN

(75) Inventor: Albert K. Chin, Palo Alto, CA (US)

(73) Assignee: Origin Medsystems, Inc., Santa Clara, CA (US)

( * ) Notice: Subject to any disclaimer, the term of this patent is extended or adjusted under 35 U.S.C. 154(b) by 103 days.

This patent is subject to a terminal disclaimer.

(21) Appl. No.: 10/638,252

(22) Filed: Aug. 7, 2003

(65) Prior Publication Data

US 2004/0030374 A1 Feb. 12, 2004

Related U.S. Application Data

(63) Continuation of application No. 09/920,194, filed on Aug. 1, 2001, now Pat. No. 6,623,514.

(51) Int. Cl.[7] ............................................... A61F 7/12
(52) U.S. Cl. ......................... 607/113; 607/96; 604/113
(58) Field of Search ........................ 607/96, 104, 105, 607/113; 604/27, 28, 113, 500, 508

(56) References Cited

U.S. PATENT DOCUMENTS

| | | | |
|---|---|---|---|
| 3,504,674 A | 4/1970 | Swenson et al. | |
| 4,666,426 A | 5/1987 | Aigner | |
| 4,840,620 A | 6/1989 | Kobayashi et al. | |
| 4,856,972 A | 8/1989 | Van Benschoten et al. | |
| 4,904,237 A | 2/1990 | Janese | |
| 5,061,241 A | 10/1991 | Stephens, Jr. et al. | |
| 5,409,547 A | 4/1995 | Watanabe et al. | |
| 5,423,807 A | 6/1995 | Milder | |
| 5,529,067 A * | 6/1996 | Larsen et al. | 600/374 |
| 5,597,377 A | 1/1997 | Aldea | |
| 5,792,094 A | 8/1998 | Stevens et al. | |
| 5,895,964 A | 4/1999 | Nakayama | |
| 5,950,067 A * | 9/1999 | Maegawa et al. | 438/22 |
| 5,954,665 A * | 9/1999 | Ben-Haim | 600/515 |
| 6,042,559 A | 3/2000 | Dobak, III | |
| 6,051,019 A | 4/2000 | Dobak, III | |
| 6,161,388 A | 12/2000 | Ghoshal | |
| 6,217,552 B1 | 4/2001 | Barbut et al. | |

\* cited by examiner

*Primary Examiner*—Roy D. Gibson
(74) *Attorney, Agent, or Firm*—Blakely, Sokoloff, Taylor & Zafman LLP

(57) ABSTRACT

A method of cooling an organ. A portion of a body fluid bathing an organ is withdrawn while a cool fluid is infused. A separate portion of the body fluid can be cooled during the withdrawing. A volume of up to about 5% of the body fluid can be withdrawn. A catheter is provided with a cooling mechanism to contact and cool the body fluid. The catheter can have an inlet port to withdraw body fluid and an outlet port to allow infusion of a cool fluid. Additionally, an organ cooling pump assembly is provided including a pump and a catheter.

14 Claims, 3 Drawing Sheets

METHOD OF COOLING AN ORGAN

BACKGROUND OF THE INVENTION

This application is a continuation application of U.S. patent application Ser. No. 09/920,194, filed Aug. 1, 2001, now U.S. Pat. No. 6,623,514.

The present invention relates to treatment of organs. In particular, the present invention relates to treatment of organs that have been subjected to trauma or ischemia.

BACKGROUND OF THE RELATED ART

When an organ has been injured or its blood supply compromised, timeliness of treatment can be critical. Organ tissue necrosis, or death, begins when the organ's blood supply is compromised and treatment is ineffective with respect to organ tissue that has died prior to treatment. Nevertheless, the time required for proper diagnosis and treatment of the organ cannot be eliminated.

The brain is no exception. Injury to the brain may result from increased pressure due to swelling of brain tissue. For example, swelling may result from internal bleeding such as from a ruptured aneurysm. Alternatively, generalized head trauma may cause swelling of brain tissue. Injury to the brain may also be the result of a lack of oxygen to brain tissue due to an embolus present within a cerebral vessel. Such an embolus can cut off an adequate blood supply to portions of brain tissue. As noted in these examples, perfusion of brain cells is compromised in both trauma and ischemia.

When brain tissue is subjected to such traumas noted above the effects as well as the need for treatment are immediate. The rate at which brain tissue dies is dependant on several factors, such as the degree of swelling or, in the case of cerebral embolism, the presence or absence of collateral vessels supplying alternative avenues of perfusion.

Treatment of the injured brain first requires a proper diagnosis. A diagnosis pinpointing the originating site of the injury can come from a computed tomography (CT) scan. From a logistical standpoint, a patient that presents, for example at an Emergency Room, with a head trauma will not likely obtain CT scan results in less than half an hour. During this critical time, brain tissue continues to die as a result of the head trauma.

Once diagnosed, the treatment chosen will take a significant amount of additional time to carry out. For example, if the brain has been subjected to an ischemic stroke, drugs such as Tissue Plasminogen Activator (TPA) may be given to the patient to help dissolve any thrombus or blood clot. Alternatively, if swelling is of concern, a hole may need to be drilled through the skull to relieve pressure on brain tissue. Additionally, more direct vascular intervention may be required. In such cases a host of catheter lab procedures may be employed. In more extreme cases, actual brain surgery may be required.

Regardless of the treatment path chosen, several hours will likely be lost during the course of the treatment. Throughout this time brain tissue will continue to die. The problem is compounded by the fact that the brain tissue cannot be regenerated.

In order to combat the problem of brain tissue death attempts have been made to curb the rate of brain tissue death. As noted above, the rate of brain tissue death is affected by factors such as the degree of swelling involved, or the overall lack of oxygen supplied to the affected tissue. Therefore, attempts to curb the rate of brain tissue death have focused on the induction of hypothermia in the patient. Hypothermia can reduce swelling. Tissue affected by hypothermia will also experience a decrease in metabolic requirements, and thus, experience a decrease in need for oxygen.

Hypothermia can be induced to reduce the core temperature of a patient. That is, the temperature of the entire body of the patient can be reduced. This can be done by reducing the temperature of the patient's blood. Reducing even a portion of the patient's blood will result in a generalized cooling of the body as the blood is carried throughout the body of the patient. However, in the case of a head trauma, a generalized reduction in the core temperature of the patient is limited in effectiveness. Reduction of a body's core temperature means that hypothermia will not be focused on the brain tissue specifically. Rather, the temperature of the brain tissue, as in the rest of the body, will be reduced by a small amount. Even if the blood of the brain is cooled directly, the focus of this cooling effect will be lost as this cooled blood, along with the remainder of the patient's blood (e.g. about 5 liters), is circulated throughout the body. In the end, a generalized core temperature reduction is the major effect obtained. This problem is applicable to any organ for which hypothermia is to be induced. Therefore, what is needed is an improved method of cooling an organ.

SUMMARY OF THE INVENTION

In one method of cooling an organ a portion of a body fluid bathing the organ is withdrawn. A cool fluid is infused during the withdrawing.

In yet another method of cooling an organ a volume of up to about 5% of a body fluid bathing the organ is withdrawn. A cool fluid is infused.

Another embodiment of a catheter is provided with an inlet port to withdraw a portion of a body fluid bathing an organ from a location adjacent the organ. An outlet port is included to infuse a cool fluid to the location as the portion of the body fluid is withdrawn.

An embodiment of an organ cooling assembly is provided including a pump assembly and a catheter coupled to the pump assembly. The catheter includes an inlet port and an outlet port. The pump is to withdraw a portion of a body fluid bathing an organ through the inlet port and to infuse a cool fluid through said outlet port.

DETAILED DESCRIPTION OF THE INVENTION

While embodiments of the present invention are described with reference to certain cooling methods, devices, and mechanisms, embodiments of the invention are applicable to any cooling system where an organ of a body is to be cooled. This would include organ cooling methods, devices, and systems directed toward cooling organs such as the brain, lungs and heart. The invention is particularly useful when the body organ to be cooled is bathed in a body fluid.

Figure 1:
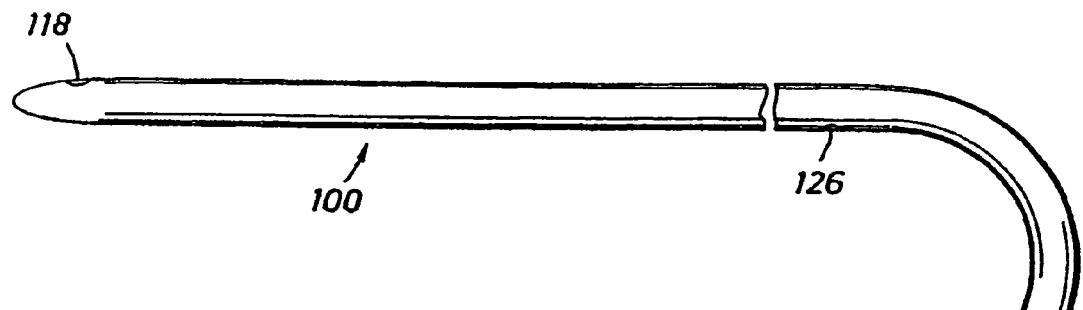
FIG. 1 is a perspective view of an embodiment of an organ cooling system of the present invention including embodiments of a catheter and a pump assembly.

Referring to FIG. 1, a catheter 100 and pump assembly 150 are shown. Embodiments of the catheter 100 can be constructed of flexible plastic materials such as polyvinyl chloride, polyethylene, nylon, polytetrafluoroethylene, and other such materials. In the embodiment shown, the catheter 100 is configured to be positioned to contact a body fluid bathing an organ. A body fluid bathing an organ is distinguished from other body fluids, such as blood, which are channeled throughout the body and not generally isolated in a region surrounding a particular organ or organs as in the case of a fluid bathing an organ.

The pump assembly 150 includes tubing 120 attached to a main body 130. The tubing 120 includes a lumen and has an intake portion 125 and an output portion 117. The tubing 120 forms a loop with the end of the intake portion 125 and the end of the output portion 117 coming together at a juncture. A portion of the tubing 120 passes through a cooling region 140 to cool any fluid contained within the lumen of the tubing 120. In the embodiment shown, the cooling region 140 includes an ice bath. However, in other embodiments of the invention, other cooling mechanisms may be included in the cooling region 140 to cool fluid within the tubing 120. For example, in one embodiment of the invention, the cooling region 140 is surrounded by a coil carrying a refrigerant to cool any fluid within the tubing 120 as it is passed through the cooling region 140.

Continuing with reference to FIG. 1, the juncture includes a joining mechanism 151 to which a proximal-most end 152 of a catheter 100 is coupled. The catheter 100 of the embodiment shown includes an outlet port 118 at the end of an output lumen 119 and an inlet port 126 at the end of an intake lumen 127. As discussed below, the catheter 100 includes cooling capacity as provided by the cooling region 140 of the pump assembly 150.

When the catheter 100 is plugged in, the joining mechanism 151 couples the end of the intake portion 125 to the intake lumen 127. The joining mechanism 151 also couple the end of the output portion 117 to the output lumen 119 of the catheter 100. In the embodiment shown, the proximal-most end 152 of the catheter 100 snaps into the joining mechanism 151 to securely position and align the catheter 100 to the tubing 120. However, in other embodiments of the invention, a luer-loc or other coupling mechanism may be employed to secure and align the catheter 100 and lumens 127, 119 to the tubing portions 125, 117. In this manner an uninterrupted lumen path from the inlet port 126, through the catheter 100, through the tubing 120, and to the outlet port 118 is provided when the catheter 100 is plugged into the pump assembly 150.

The embodiment of pump assembly 150 shown includes a roller assembly 103. The pump assembly 150 is operated by the roller assembly 103 rotating and contacting the tubing 120. The tubing 120 is held in place by a support roller 105 as the roller assembly 103 contacts the tubing 120. During rotation of the roller assembly 103, the portion of the tubing 120 contacted by the roller assembly 103 is intermittently compressed and relaxed between the roller assembly 103 and the support roller 105. In this manner, any fluid present within the tubing 120, and therefore, the uninterrupted lumen path discussed above, is circulated.

The amount of fluid pumped per rotation of the roller assembly 103 can be determined based on the size of the tubing 120 used, the amount of compression obtained during a rotation of the roller assembly 103, and the length of contact between the roller assembly 103 and the tubing 120 during a rotation of the roller assembly 503. Therefore, the roller assembly 103 can be configured and directed with a particular exchange or cooling method in mind (see FIGS. 7 and 8).

The roller assembly 103 which acts to compress the tubing 120, discussed above, is driven by a motor drive unit. The motor drive unit rotates the roller assembly 103 based on a control signal received. The control signal is established by an operator of the pump assembly 150, for example, at a control panel coupled to the pump assembly 150. The roller assembly 103 will rotate according to a particular fluid exchange or cooling method to be employed as directed by the operator (see FIGS. 7 and 8).

Figure 2:
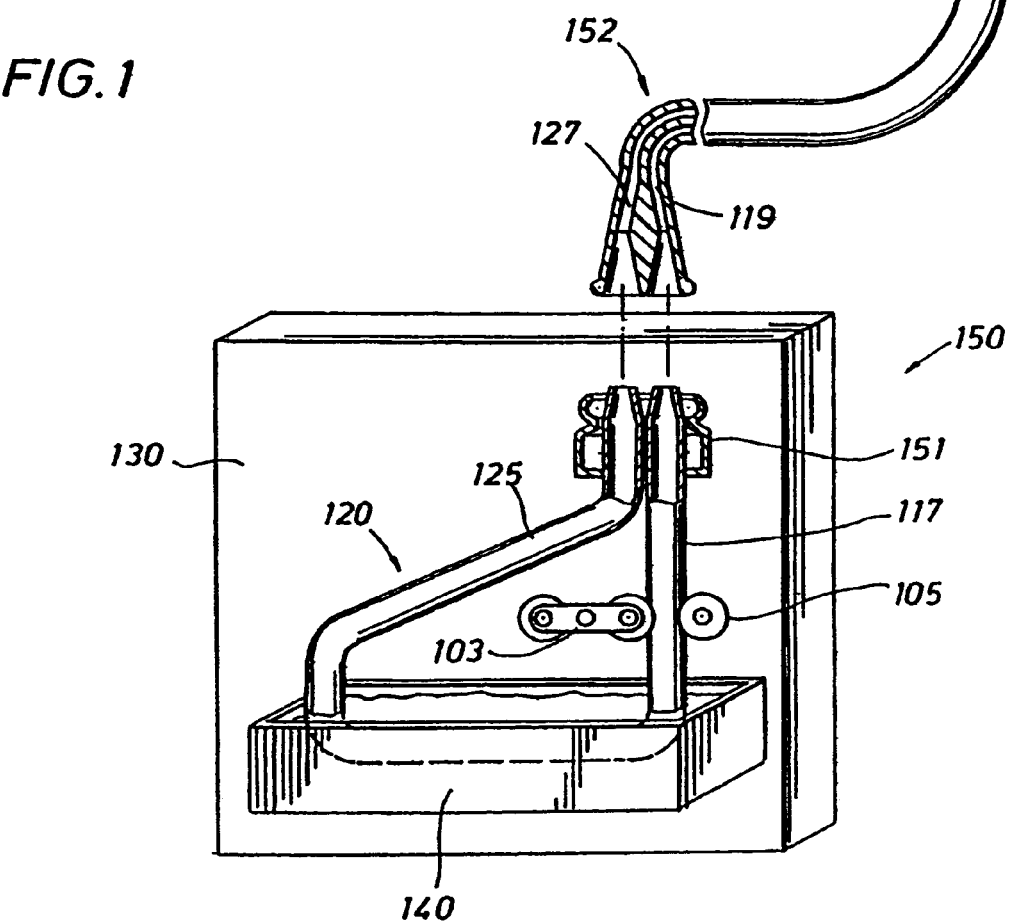
FIG. 2 is a longitudinal cross-sectional view of the catheter of FIG. 1.
Figure 2:
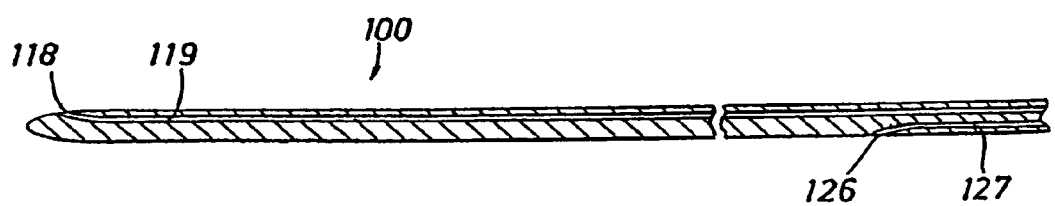

Referring to FIG. 2, a longitudinal cross-sectional view of the catheter 100 of FIG. 1 is shown. The output lumen 119 is shown throughout the catheter 100 terminating at outlet port 118. The intake lumen 125 is shown terminating more proximally at inlet port 126.

Figure 3:
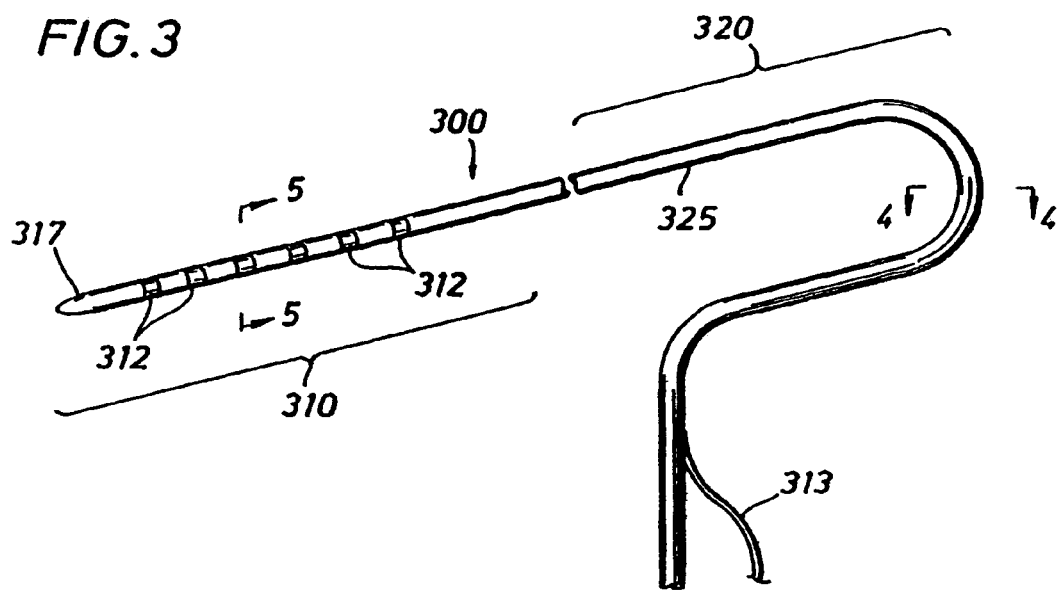
FIG. 3 is a perspective view of an embodiment of a catheter of the present invention.

Referring to FIG. 3, an alternate embodiment of catheter 300 is shown. In the embodiment of FIG. 3, the distal portion 310 of the catheter 300 includes a cooling mechanism. In the embodiment shown, the cooling mechanism includes cooling elements 312. In one embodiment of the invention, discussed further herein, the cooling elements 312 are thermoelectric cooling chips which, when activated, absorb heat from a surrounding environment to cool the surrounding environment. An insulated lead 313 is coupled to the catheter 300 at the proximal portion 320 to electronically couple a power source to the cooling elements 312 as also discussed further herein.

The distal portion 310 of the catheter 300 embodiment shown also includes an outlet port 317 from which a cool fluid can be dispensed. The proximal portion 320 of the catheter 300 includes an inlet port 325 through which a fluid can be drawn into the catheter. In one embodiment of the invention, also discussed further herein, where the catheter 300 is to be inserted within a spinal canal 700 (see FIG. 7), the inlet port 325 is positioned from about 5 cm to about 25 cm from the outlet port 317, preferably from about 10 cm to about 20 cm.

Figure 4:
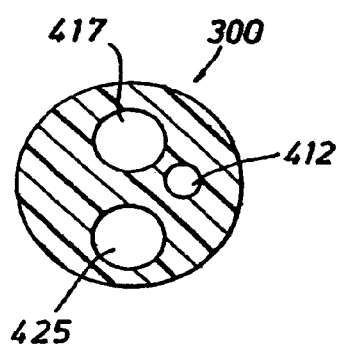
FIG. 4 is a cross-sectional view of the catheter of FIG. 3 taken from section line 4—4 of FIG. 3.
Figure 5:
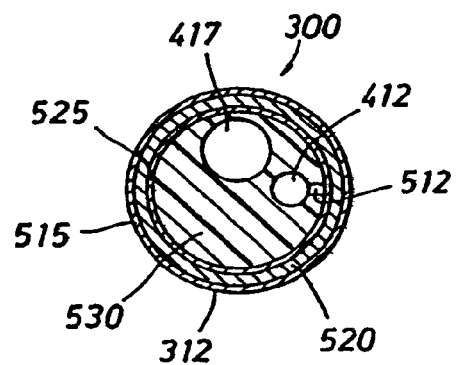
FIG. 5 is a cross-sectional view of the catheter of FIG. 3 taken from section line 5—5 of FIG. 3.

Referring to FIGS. 3–5, cross sectional views, taken from section lines 4—4 and 5—5, of the catheter 100 of FIG. 1 are shown. FIG. 4 reveals an intake lumen 425 not present in FIG. 5. This is because the intake lumen 425 does not run through the distal portion 310 of the catheter 300. The inlet port 325 leads to the intake lumen 425 which runs proximally from the inlet port 325 to a proximal-most end of the catheter 300. FIG. 4 also reveals an output lumen 417. The outlet port 317, shown in FIG. 3, leads to the output lumen 417 which runs proximally from the outlet port 317 to a proximal-most end of the catheter 300.

Continuing with reference to FIGS. 3–5, the catheter 300 also includes a cooling lumen 412. The cooling lumen 412 runs interior of the catheter 300 from the insulated lead 313 to a position within the distal portion 310 of the catheter 300. In the embodiment shown, the cooling lumen 412 carries electrical wire from the insulated lead 313 to the cooling elements 312. In other embodiments of the invention, where other cooling mechanisms are employed, the cooling lumen 412 carries other supportive cooling features.

Referring to FIG. 5, the cooling lumen 412 of the embodiment shown is electrically coupled to each cooling element 312 of the distal portion 310 of the catheter 300 (see FIG. 3) through a via 512. In this manner, electrical wire can be carried directly to each cooling element 312.

Continuing with reference to FIG. 5, each cooling element 312 achieves temperature differential by the Peltier effect. That is, each cooling element 312 has a semiconductor layer 520 disposed between a heat absorbing layer 515 and a heat dissipating layer 525. The heat absorbing layer 515 includes a heat absorbing electrode and insulating substrate. The heat dissipating layer 525 includes a heat dissipating electrode and insulating substrate. As a current from a power source reaches each cooling element 312 the heat absorbing layer 515 begins to absorb heat which is dissipated interior of the catheter 300 from the heat dissipating layer 525. To further dissipation, heat sinks from the heat dissipating layer 525 and into the catheter interior 530 can be provided. A cooling element 312 as described can be placed in contact with a body fluid and activated to cool the body fluid (see FIGS. 7 and 8). The heat absorbing layer 515 of the cooling element is of a biocompatible material or covered by a biocompatible material for contacting a body fluid.

Figure 6:
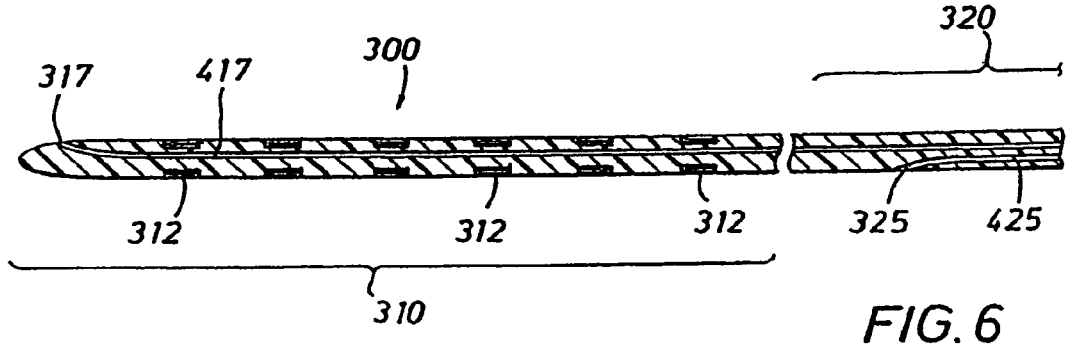
FIG. 6 is a longitudinal cross-sectional view of the catheter of FIG. 3.

Referring to FIG. 6, a longitudinal cross-sectional view of the catheter 300 of FIG. 3 is shown. The cooling elements 312 are shown disposed in the distal portion 310 of the catheter 300. The output lumen 417 is shown through both the proximal 320 and distal 310 portions of the catheter 300, and terminating at the outlet port 317. The intake lumen 325 is shown running to within the proximal portion 320 of the catheter 300 and terminating at the inlet port 325. The catheter 300 may be coupled to a pump assembly 150 (as shown in FIG. 1) to pump fluids through the intake lumen 425 or output lumen 417 as a body organ is cooled (see FIGS. 7 and 8).

Figure 7:
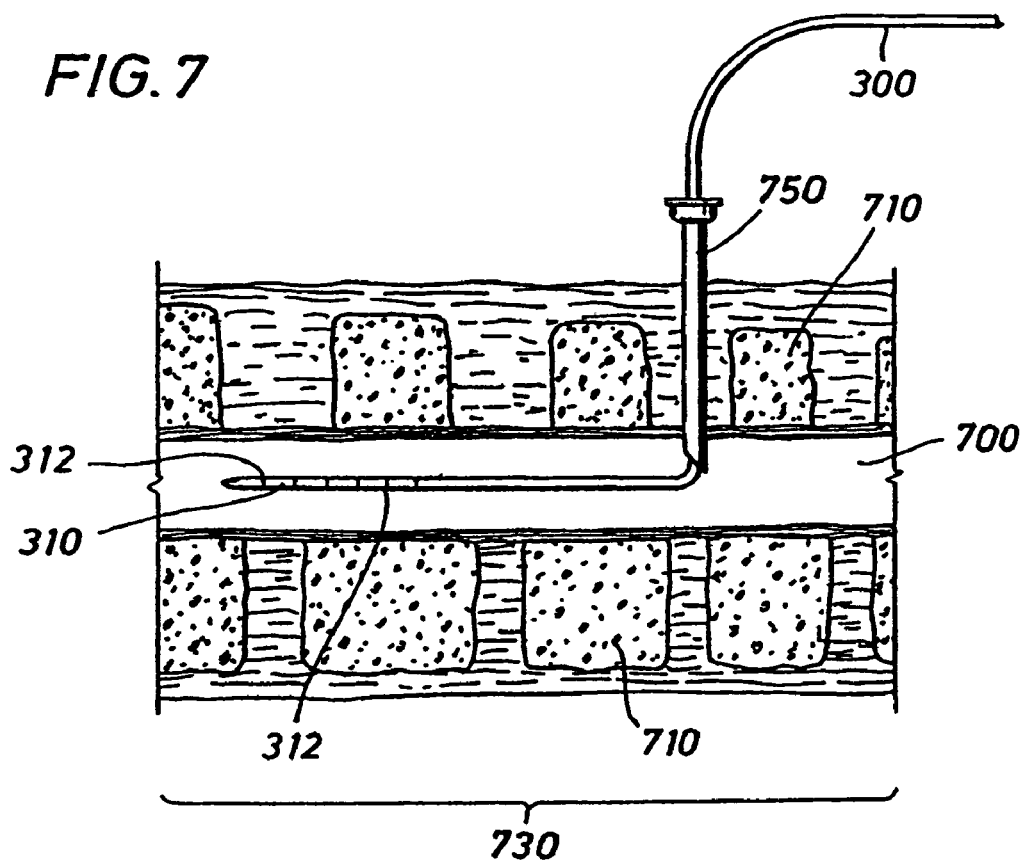
FIG. 7 is a side view of the catheter of FIG. 3 inserted within a patient to contact a fluid bathing an organ.

Referring to FIG. 7, a method of the invention is described where the catheter 300 of FIG. 3 is inserted into a body of a patient to an area containing a body fluid bathing an organ. In the embodiment shown, the catheter 300 is inserted into the spinal canal 700 of the patient where cerebrospinal fluid (CSF) is found. The catheter 300 is inserted at this location to treat the brain of the patient. The catheter 300 has an outer diameter of between about 0.7 mm and about 1.3 mm, preferably between about 0.9 mm and about 1.1 mm.

The CSF bathes the brain of the patient. CSF, as with other fluids bathing organs, is not circulated throughout the body of the patient. Rather, the CSF is found only in the spinal canal and surrounding the brain of the patient. Therefore, as described below, cooling of the CSF can act to cool the brain of the patient without losing the cooling effect, via circulation, to the rest of the body. Additionally, only about 70 cc to about 120 cc of CSF is present within the patient. Therefore, a lower total volume of fluid (e.g. CSF) can be cooled to induce hypothermia of the brain.

Continuing with reference to FIG. 7, a spinal needle 750 is shown inserted between vertebrae 710 of the lumbar region 730 of a patient to provide access to the patient's spinal canal 700. In other embodiments of the invention, the spinal needle 750 is inserted between vertebrae 710 in other regions of the spine. The catheter 300 is inserted through the spinal needle 750 and into the spinal canal 700. In one embodiment of the invention, the cooling elements 312 of the distal portion 310 of the catheter 300 are activated to begin cooling CSF within the spinal canal 700 immediately upon contacting the CSF. The catheter 300 is advanced within the spinal canal 700 toward the cervical region 830 (see FIG. 8) of the spinal canal 700. In one embodiment of the invention, the catheter 300 is advanced over a pre-positioned guidewire in the spinal canal 700. However, a guidewire is not required for the catheter 300 to reach the spinal canal 700 or for advancement to the cervical region 830.

In the embodiment shown the catheter 300 is coupled to the pump assembly 150 of FIG. 1. Thus, as described further herein, cooling of CSF occurs directly through contact with the cooling elements 312 and once pumped through the cooling region 140 of the pump assembly 150 shown in FIG. 1. However, in other embodiments of the invention, the cooling elements 312 or the cooling region 140 alone can be used to cool the CSF.

Figure 8:
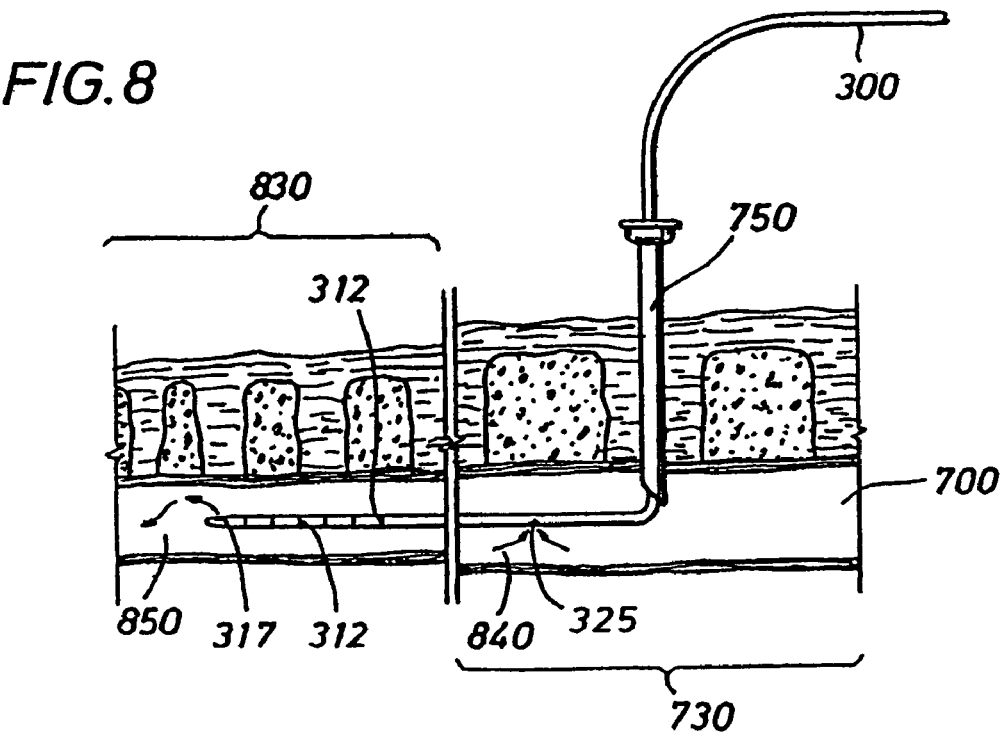
FIG. 8 is a side view of the catheter of FIG. 3 inserted within a patient and contacting separate portions of a fluid bathing an organ.

Referring to FIG. 8, the catheter 300 has been advanced as far distally as possible to within the cervical region 830 of the spinal canal 700, adjacent the brain of the patient. CSF within the cervical region 830 filters through the spinal canal 700 to bathe the brain of the patient. The inlet port 325 of the catheter 300 remains within the lumbar region 730 of the spinal canal 700 whereas the outlet port 317 of the catheter 300 is found within the cervical region 830 of the spinal canal 700. The cooling elements 312 as shown are cooling CSF within the cervical region 830 of the spinal canal.

Continuing with reference to the embodiment of FIG. 8, the pump assembly 150 (shown in FIG. 1), to which the catheter 300 is attached, is activated to draw in warm CSF 840 through the inlet port 325 and expel cool CSF 850 through the outlet port 317. The amount of CSF drawn in is substantially equivalent to the amount expelled. In one embodiment of the invention, only up to about 5% of the total volume of CSF is exchanged per pump compression in this manner, preferably between about 2% and about 3%. Such an exchange helps ensure a stable pressure within the spinal canal 700 during induction of hypothermia. To further ensure efficient cooling and stable pressure, in one embodiment of the invention, the pump 150 and roller 103 assemblies (shown in FIG. 1) are configured to pump between about 1.5 cc and about 3.5 cc per compression, preferably between about 2.0 and about 3.0 cc. Additionally, in another embodiment of the invention, the assemblies 150, 103 are configured to pump from about 130 cc to about 230 cc per minute, preferably between about 170 cc and about 190 cc.

In one embodiment of the invention, the catheter 300, and tubing 120 are initially filled with cool saline. The cool saline is expelled prior to cool CSF 850 to prevent pressure changes or the influx of air or gas to within the spinal canal 700 when CSF has yet to circulate through the system to reach the outlet port 317.

Warm CSF 840 is taken to the pump assembly 150 where it is initially cooled by the cooling region 120 (shown in FIG. 1). The CSF is then cool CSF 850 which travels through the tubing 120 (shown in FIG. 1) and back through the catheter 300 where it exits at the outlet port 317. The cooling elements 312 continue to cool the cool CSF 850 once it is emptied into the cervical region 830 of the spinal canal 700 from the output port 317.

In the embodiment shown, warm CSF 840 is that portion of CSF which is still to be cooled as discussed above. By distancing the inlet port 325 away from the outlet port 317 and within the lumbar region 730, hypothermia can be focused on the cervical region 830 from where CSF is to be filtered to bathe the brain of the patient to induce hypothermia of the brain. However, positioning of the ports 317, 325 in this manner is not required in order to cool the CSF to induce hypothermia of the brain. In another embodiment of the invention, the patient is placed in the Trendelenburg position, with the lower limbs elevated to a position higher than the heart, during cooling of the CSF to aid in the transfer of cool CSF 850 from the spinal canal 700 to surround the brain.

As described above, hypothermia is induced in the brain by cooling CSF in which the brain is bathed. The CSF within the spinal canal 700 continually diffuses beyond the cervical region 830 to directly contact the brain. In fact, a complete transfer of the total volume of CSF within the spinal canal 700 is exchanged with CSF directly bathing the brain several times each day. Therefore, cooling of the CSF within the spinal canal 700 can be used to begin the process of hypothermia induction in an immediate manner.

In embodiments of the invention described above, CSF within the spinal canal 700 is cooled in order to induce hypothermia of the brain. Cooling CSF in this manner requires only the simple placement of a spinal needle 750 and insertion of the catheter 300 there through in order for cooling to begin. Access to the CSF is readily available in the spinal canal 700. Placement of a spinal needle 750 does not require fluoroscopic control and the patient does not need to be brought to an X-ray suite. Therefore, embodiments of the invention can be quickly applied to save brain tissue prior to moving forward with additional treatment and/or diagnosis.

Employing embodiments of the invention allows time to be saved, hypothermia to be induced, and brain cells to be saved when a patient presents with a head trauma. Additionally, the organ hypothermia induces is focused on the brain and the cooling effect is not redistributed throughout the body. Therefore, the efficiency of the cooling is increased and the amount of brain tissue saved is optimized.

In other embodiments of the invention, other organs are cooled by cooling fluids, or portions of fluids, in more direct contact with the organs to be cooled. For example, in one embodiment of the invention, a catheter is inserted to within the pericardium, containing pericardial fluid, to treat a patient's heart. In this embodiment, pericardial fluid in direct contact with the heart is cooled to induce hypothermia in the heart. In another embodiment of the invention, a catheter is inserted to within the pleura, containing pleural fluid, to treat a lung of a patient. Again, in this embodiment, pleural fluid in direct contact with the lung is cooled to induce hypothermia in the lung.

Embodiments of the invention include an improved method for cooling an organ. Although exemplary embodiments of the invention describe particular hypothermia treatments with respect to the brain of a patient, additional embodiments of the invention are possible. For example, in other embodiments of the invention a catheter is advanced to areas containing other body fluids to treat other organs of the patient. Additionally, many changes, modifications, and substitutions may be made without departing from the spirit and scope of this invention.

I claim:

1. A catheter, comprising:
   a first catheter portion having an inlet port to withdraw a portion of a body fluid bathing an organ from a first region of a location adjacent the organ;
   a second catheter portion having an outlet port to infuse a cool fluid to a second region of the location as the portion of the body fluid is withdrawn; and
   one or more cooling elements disposed along a distal portion of the catheter for cooling the body fluid, wherein the location is selected from a group consisting of a spinal canal, a pericardium, and a pleura.

2. The catheter of claim 1, further comprising an outer diameter of between about 0.7 mm and about 1.3 mm.

3. The catheter of claim 1, wherein the inlet port is distanced from about 5 cm to about 25 cm from the outlet port along a body of the catheter.

4. The catheter of claim 1, wherein the body fluid is selected from a group consisting of cerebrospinal fluid, pericardial fluid, and pleural fluid.

5. The catheter of claim 1, wherein the organ is selected from a group consisting of a brain, a heart, and a lung.

6. The catheter of claim 1, wherein the cool fluid is selected from a group consisting of cool saline and said body fluid in a cooled state.

7. The catheter of claim 1, wherein the location is a spinal canal, the first region is a lumbar region of the spinal canal and the second region is a cervical region of the spinal canal.

8. The catheter of claim 1, further comprising a cooling lumen within the catheter, wherein the one or more cooling elements are controlled by an electronic lead coupled to a proximal portion of the catheter via the cooling lumen.

9. The catheter of claim 1, wherein the one or more cooling elements comprise thermoelectric cooling chips.

10. An organ cooling assembly, comprising:
    a pump assembly; and
    a catheter coupled to said pump assembly, the catheter having an inlet port and an outlet port, the pump assembly to withdraw a portion of a body fluid bathing an organ through the inlet port from a first region of a location adjacent said organ and to infuse a cool fluid to a second region of the location through the outlet port as the portion of said body fluid is withdrawn,
    wherein said catheter includes one or more cooling elements disposed along a distal portion of the catheter for cooling said body fluid, wherein the location is selected from a group consisting of a spinal canal, a pericardium, and a pleura.

11. The organ cooling assembly of claim 10, wherein the pump assembly includes a cooling device to cool the portion of the body fluid.

12. The organ cooling assembly of claim 11, wherein the cooling device is selected from a group consisting of a cooling jacket with a refrigerated coil and an ice bath.

13. The organ cooling assembly of claim 10, wherein the catheter further comprises a cooling lumen therein, wherein the one or more cooling elements are controlled by an electronic lead coupled to a proximal portion of the catheter via the cooling lumen.

14. The organ cooling assembly of claim 10, wherein the one or more cooling elements comprise thermoelectric cooling chips.

* * * * *